(12) United States Patent
Eisinger et al.

(10) Patent No.: US 8,852,541 B2
(45) Date of Patent: Oct. 7, 2014

(54) SYSTEMS AND METHODS FOR REMOVING IMPURITIES FROM A FEED FLUID

(75) Inventors: Ronald S. Eisinger, Charleston, WV (US); David M. Gaines, St. Albans, WV (US)

(73) Assignee: Univation Technologies, LLC, Houston, TX (US)

( * ) Notice: Subject to any disclaimer, the term of this patent is extended or adjusted under 35 U.S.C. 154(b) by 588 days.

(21) Appl. No.: 12/922,603

(22) PCT Filed: Apr. 16, 2009

(86) PCT No.: PCT/US2009/002368
§ 371 (c)(1),
(2), (4) Date: Sep. 14, 2010

(87) PCT Pub. No.: WO2009/145851
PCT Pub. Date: Dec. 3, 2009

(65) Prior Publication Data
US 2011/0027156 A1 Feb. 3, 2011

Related U.S. Application Data

(60) Provisional application No. 61/124,482, filed on Apr. 17, 2008.

(51) Int. Cl.
*B01D 53/62* (2006.01)
*B01D 53/72* (2006.01)
(Continued)

(52) U.S. Cl.
CPC ............... *C10G 25/05* (2013.01); *B01J 37/084* (2013.01); *B01J 29/06* (2013.01); *B01J 23/72* (2013.01); *C07C 7/14841* (2013.01); *B01J 37/18* (2013.01); *B01J 20/28052* (2013.01); *B01J 23/94* (2013.01); *Y02C 10/04* (2013.01); *C10G 2300/1092* (2013.01); *B01J 20/10* (2013.01); *B01D 15/00* (2013.01); *C07C 7/005* (2013.01); *C10G 2300/201* (2013.01); *C07C 7/12* (2013.01); *B01J 20/18* (2013.01)
USPC ............... 423/219; 423/23; 423/42; 423/220; 423/245.1; 423/700

(58) Field of Classification Search
USPC .................... 423/23, 42, 219, 220, 245.1, 700
See application file for complete search history.

(56) References Cited

U.S. PATENT DOCUMENTS 2,837,587 A 6/1958 Paul et al.
3,676,516 A 7/1972 Haskell et al.
(Continued)

FOREIGN PATENT DOCUMENTS

EP 0966508 12/1999
GB 907158 10/1962
WO WO 2006/076096 7/2006

OTHER PUBLICATIONS

Katz, Morris, "Heterogeneous Oxidation of Carbon Monoxide," in Advances in Catalysis, vol. V, p. 177 (1953).

*Primary Examiner* — Stanley Silverman
*Assistant Examiner* — Daniel Berns
(74) *Attorney, Agent, or Firm* — Leandro Arechederra, III; Kristina Leavitt; Jennifer A. Schmidt (57) ABSTRACT

Systems and methods for removing impurities from a feed fluid in a single vessel. A method generally includes, in single vessel, contacting a feed fluid passing through the vessel with a copper-based material for removing oxygen from the feed fluid; and contacting the feed fluid passing through the vessel with an adsorbent for removing at least one of water, carbon dioxide, and oxygenated hydrocarbons from the feed fluid.

13 Claims, 3 Drawing Sheets

(51) Int. Cl.
   *B01D 53/46* (2006.01)
   *B01D 53/02* (2006.01)
   *B01D 53/86* (2006.01)
   *B01J 37/08* (2006.01)
   *C10G 25/05* (2006.01)
   *B01J 29/06* (2006.01)
   *B01J 23/72* (2006.01)
   *C07C 7/148* (2006.01)
   *B01J 37/18* (2006.01)
   *B01J 20/28* (2006.01)
   *B01J 23/94* (2006.01)
   *B01J 20/10* (2006.01)
   *B01D 15/00* (2006.01)
   *C07C 7/00* (2006.01)
   *C07C 7/12* (2006.01)
   *B01J 20/18* (2006.01)

(56) References Cited

U.S. PATENT DOCUMENTS

| | | |
|---|---|---|
| 4,025,321 A | 5/1977 | Anderson et al. |
| 4,233,038 A | 11/1980 | Tao |
| 4,765,808 A * | 8/1988 | Oigo et al. .................. 95/140 |
| 4,784,672 A | 11/1988 | Sircar |
| 5,157,204 A | 10/1992 | Brown et al. |
| 5,446,232 A * | 8/1995 | Chen et al. .................. 585/845 |
| 5,447,558 A | 9/1995 | Acharya |
| 5,907,076 A | 5/1999 | Ou et al. |
| 6,069,288 A | 5/2000 | Ou et al. |
| 6,124,517 A | 9/2000 | Kaminsky et al. |
| 6,168,769 B1 | 1/2001 | Zisman et al. |
| 6,278,033 B1 | 8/2001 | Flick et al. |
| 6,680,419 B2 | 1/2004 | Satek et al. |
| 6,987,152 B1 | 1/2006 | Eisinger et al. |
| 7,314,965 B2 | 1/2008 | Vorberg et al. |
| 2003/0105376 A1 | 6/2003 | Foral et al. |
| 2003/0105379 A1 | 6/2003 | Bahr et al. |
| 2003/0114296 A1 | 6/2003 | Gislason et al. |
| 2003/0200866 A1 | 10/2003 | Weyrich et al. |
| 2004/0045434 A1 | 3/2004 | Golden et al. |
| 2005/0241478 A1* | 11/2005 | Junicke et al. .................. 95/140 |
| 2005/0265912 A1 | 12/2005 | Alvarez, Jr et al. |
| 2007/0023325 A1 | 2/2007 | Kumar et al. |

* cited by examiner

SYSTEMS AND METHODS FOR REMOVING IMPURITIES FROM A FEED FLUID

CROSS-REFERENCE TO RELATED APPLICATIONS

This application is a National Stage application under 36 U.S.C. §371 of International Application No. PCT/US2009/02368, filed Apr. 16, 2009, that claims the benefit of Ser. No. 61/124,482, filed Apr. 17, 2008, the disclosures of which are incorporated by reference in their entireties.

FIELD OF THE INVENTION

The invention generally relates to the removal of impurities from feed fluids, such as, for example, polyolefin feed streams. In particular, this disclosure relates to the removal of carbon monoxide, carbon dioxide, oxygen, and/or water from feed fluids in a single vessel at ambient temperature.

BACKGROUND

Newer polymerization catalysts have the unique ability to produce polymers having product properties that have not been previously obtained. Those polymerization catalysts are typically expensive and highly sensitive to impurities in the feed streams. Impurities in the feed streams poison or otherwise affect the polymerization catalysts, thereby significantly decreasing the catalyst activity and performance. As such, the presence of impurities dramatically increases production costs and is a detriment to product quality. There is a need, therefore, for a cost-effective way to remove impurities in the feed streams prior to polymerization.

Processes that polymerize olefins, for example, ethylene, propylene, butene, hexene, octene, etc. often use high-activity catalysts that may be sensitive to poisons in the polymerization feed stream. Common poisons that decrease catalyst activity or cause operating problems in the polymerization process include, among others, oxygen ($O_2$) and carbon monoxide (CO). Copper (Cu) in its various oxidation states, particularly copper oxide (CuO), is useful for removing certain poisons, such as carbon monoxide, through catalytic oxidation of carbon monoxide to carbon dioxide ($CO_2$). However, the oxidation of carbon monoxide by copper oxide is typically accomplished at temperatures well above ambient temperature to effectively remove the carbon monoxide. For example, a review in Katz, Morris, "Heterogeneous Oxidation of Carbon Monoxide," in *Advances in Catalysis*, vol. V, p. 177 (1953), indicates that the oxidation of carbon monoxide by unpromoted copper oxide may not commence until about 200° C. (392° F.).

Purification processes may require heating and cooling the feed olefin to effectively remove the catalyst poisons from the olefin feed, thus, consuming significant energy to process the feed olefin. For example, a reactor system may receive olefins at about ambient temperatures—e.g., about 0° C. (32° F.) to about 35° C. (95° F.). The olefin purification train has individual stages for removal of oxygen and carbon monoxide followed by a vessel having an adsorbent bed(s) for removal of water and carbon dioxide. The oxygen and carbon monoxide removal beds typically operate at about 100° C. (212° F.) or higher, while the adsorbent beds typically operate at ambient temperatures. This means the feed olefin must first be heated to 100° C. (212° F.) or higher prior to oxygen removal then cooled again to near-ambient temperatures thereafter and prior to contacting the adsorbent bed(s).

One catalyst known for removing carbon monoxide is a mixture of copper oxide and manganese dioxide known as hopcalite. Some hopcalite catalysts are thought to remove carbon monoxide from dry air by reaction at ambient temperature as low as −20° C. (−4° F.). U.S. Pat. No. 2,837,587 discusses the removal of carbon monoxide from a mixture of olefins and hydrogen at about 10° C. (50° F.) to about 90° C. (194° F.) and at space velocity up to about 1000 $h^{-1}$ with a hopcalite catalyst. However, hopcalite may hydrogenate some olefins, such as ethylene, making it undesirable for many polyolefin polymerization processes.

U.S. Pat. No. 5,907,076 discloses a copper oxide catalyst to oxidize hydrogen and carbon monoxide contained in a hydrocarbon stream at a temperature as low as about 40° C. (104° F.). The Examples of the '076 patent demonstrate an oxidation temperature of about 104° C. (219° F.). The '076 patent indicates multiple scenarios of operation. In one scenario, the carbon monoxide is reacted with less than a stoichiometric amount of oxygen, which results in little oxygen passing through the removal bed, but some carbon monoxide passing through the removal bed. In a subsequent step, the remaining carbon monoxide is removed by reacting carbon monoxide and water over a separate metal oxide catalyst to form carbon dioxide. In another scenario, the stream is denuded of carbon monoxide by reacting the carbon monoxide with a copper oxide catalyst with 100% to 500% of the stoichiometric amount of oxygen present, but allows for oxygen passing through the removal bed.

EP 0 966 508 A discusses a process comprising at least two steps for removing impurities, such as oxygen, in an olefin stream. The first step teaches the hydrogenation of oxygen and other impurities using a hydrogenation catalyst containing silver and palladium. The second step teaches removing at least part of the residual oxygen by oxidation with carbon monoxide with a copper/copper oxide catalyst. The disclosure indicates that during the reaction of carbon monoxide and oxygen, the temperature should be at least about 15° C. (59° F.) and preferably about 40° C. (104° F.) or more.

Other background references include U.S. Pat. Nos. 3,676,516; 4,025,321; 4,233,038; 4,784,672; 5,157,204; 5,447,558; 6,069,288; 6,124,517; 6,168,769; 6,680,419; 6,987,152; 7,314,965; U.S. Application Nos. 2003/0105376; 2003/0105379; 2003/0200866; 2004/0045434 and WO 2006/076096.

SUMMARY

In a class of embodiments, the invention provides for a method for removing impurities from a feed fluid, the feed fluid comprising primarily a hydrocarbon is provided in one general embodiment. The method comprises, in a single vessel, contacting a feed fluid passing through the vessel with a copper-based material for removing oxygen and/or carbon monoxide from the feed fluid; and contacting the feed fluid passing through the vessel with an adsorbent for removing at least one or more of water, carbon dioxide, and oxygenated hydrocarbons from the feed fluid. As an option, additional oxygen may be added to the feed fluid to assist in removal of carbon monoxide.

In another class of embodiments, the invention provides for a system for removing impurities from a feed fluid, the feed fluid comprising primarily a hydrocarbon is provided in another general embodiment. The system comprises a vessel having an inlet and an outlet; a copper-based material in the vessel, the copper-based material being for removing oxygen from a feed fluid entering the vessel through the inlet; and an adsorbent in the vessel, the adsorbent being for removing at least one of water, carbon dioxide, and oxygenated hydrocarbons from the feed fluid passing through the vessel.

In yet another class of embodiments, the invention provides for a method for regenerating a system for removing impurities from a feed fluid, the feed fluid comprising primarily a hydrocarbon is provided in yet another general embodiment. The method comprises contacting an oxidized copper-based material and an adsorbent in a single vessel with an inert gas heated to a first temperature above an ambient temperature for removing hydrocarbon adsorbed thereon; adding a reducing agent to the heated inert gas for reducing the copper-based material; increasing a concentration of reducing agent added in the heated inert gas contacting the copper-based material and the adsorbent; heating the inert gas and the reducing agent to a second temperature higher than the first temperature; and contacting the copper-based material and the adsorbent with the inert gas and the reducing agent at the second temperature.

In still another class of embodiments, the invention provides for a method for removing impurities from a feed fluid comprising primarily a non-carbonaceous gas is provided in one general embodiment. The method comprises, in a single vessel, contacting a feed fluid passing through the vessel with a copper-based material for removing oxygen from the feed fluid; and contacting the feed fluid passing through the vessel with an adsorbent for removing at least one of water and carbon dioxide from the feed fluid.

DETAILED DESCRIPTION

Before the present compounds, components, compositions, devices, softwares, hardwares, equipments, configurations, schematics, systems, and/or methods are disclosed and described, it is to be understood that unless otherwise indicated this invention is not limited to specific compounds, components, compositions, devices, softwares, hardwares, equipments, configurations, schematics, systems, methods, or the like, as such may vary, unless otherwise specified. It is also to be understood that the terminology used herein is for the purpose of describing particular embodiments only and is not intended to be limiting.

It must also be noted that, as used in the specification and the appended claims, the singular forms "a," "an" and "the" include plural referents unless otherwise specified.

Generally, embodiments disclosed herein relate to methods of removing impurities from a feed fluid comprising primarily a hydrocarbon in a single vessel. For example, embodiments disclosed herein relate to systems and methods for removing carbon monoxide, carbon dioxide, oxygen, and water from a feed stream to a polymerization process in a single vessel while the feed stream is near or at ambient temperatures.

Other general embodiments include methods for regenerating a system for removing impurities from a feed fluid. The embodiments herein further relate to methods of regenerating a system capable of performing the aforementioned removal of impurities from a feed fluid in a single vessel.

The term "impurities" as used herein refers to a component or compound that reduces the activity of a polymerization catalyst or adversely affects an olefin polymerization process. Illustrative impurities include, but are not limited to, oxygen, carbon monoxide, carbon dioxide, hydrocarbons having oxygen-containing functional groups such as, for example, alcohols, aldehydes, ketones, organic acids, some esters and peroxides, water, sulfur-containing compounds, and arsine. Illustrative sulfur-containing compounds include, but are not limited to hydrogen sulfide, carbonyl sulfide, and mercaptans having the general formula R—SH where R is an alkyl group having 1 to 20 carbon atoms.

The term "feed fluid" as used herein refers to a raw material, either gas phase or liquid phase. For example such raw material, when purified as described herein, may be stored optionally for a later use, used in a polymerization process producing a polymer product, etc. For example, a feed fluid may include any olefin monomer including substituted and unsubstituted alkenes having two to 10 carbon atoms, such as ethylene, propylene, 1-butene, 1-pentene, 1-hexene, 1-octene, 1-decene, 1-dodecene, styrene, and derivatives, and mixtures thereof. The feed fluid may also include or be comprised primarily of a gas stream such as nitrogen, hydrogen, etc. The feed fluid may further include one or more nonreactive alkanes that are condensable in the polymerization process for removing the heat of reaction. Illustrative nonreactive alkanes include, but are not limited to, propane, butane, isobutane, pentane, isopentane, hexane, isomers thereof, and derivatives thereof.

The term "packed bed" as used herein refers to a bed of material for impurity removal (i.e. "purification material") that is disposed within a container or vessel. A packed bed may comprise one or more catalysts, absorbents, adsorbents, reactants, and any combination thereof. A packed bed may be contained in a single container, such as a vertical pressure-rated vessel, or may be split between two or more contiguous vessels. Also, a packed bed may contain more than one layer of purification materials in a single container or vessel. The term "single packed bed" refers to a contiguous bed of one purification material in a packed bed. In other words, the feed fluid only passes through the purification material at one step in a series of purification steps. The term "single packed bed" also includes two or more packed beds of the same purification material arranged in parallel.

The term "adsorbent" as used herein refers to either a single purification material that adsorbs impurities or to two or more different purification materials that adsorb impurities.

The term "space velocity" (SV) as used herein refers to the volumetric flow rate of a fluid through a packed bed at standard conditions divided by the volume of the packed bed. Standard conditions are 1 atmosphere of pressure and a temperature of 21° C. (70° F.). All values of SV herein are expressed in units of $h^{-1}$ (inverse hours).

The term "ambient temperature" as used herein refers to the temperature of the environment in which any physical or chemical event occurs, unless otherwise specified. The term "at" or "near" "ambient temperature" as used herein refers to the temperature of the environment in which any physical or chemical event occurs plus or minus ten degrees, alternatively, five degrees, alternatively, three degrees, alternatively two degrees, and alternatively, one degree, unless otherwise specified. A typical range of ambient temperatures is between about 0° C. (32° F.) and about 40° C. (104° F.), though ambient temperatures could include temperatures that are higher or lower than this range.

All concentrations expressed herein are concentrations in terms of parts per million by volume unless otherwise stated.

It has been surprisingly discovered that carbon monoxide, oxygen, oxygenated hydrocarbons, and water can be removed from a feed fluid stream in a single vessel while the stream is at temperatures of less than about 40° C. (104° F.) by passing the stream over a reduced copper-based material in the presence oxygen and carbon monoxide, and then passing the stream over an adsorbent. Particularly surprising is the finding that the carbon monoxide, oxygen, and water can be removed to levels of less than about 0.2 ppm by volume at temperatures of less than about 40° C. (104° F.) in a single vessel through this method. Most surprisingly, it has been found that all purification materials in the vessel can be regenerated under a single set of conditions.

In one general embodiment, a method for removing impurities from a feed fluid comprising primarily a hydrocarbon in a single vessel comprises contacting a feed fluid passing through the vessel with a copper-based material for removing oxygen from the feed fluid, the feed fluid comprising primarily a hydrocarbon; and contacting the feed fluid passing through the vessel with an adsorbent for removing at least one of water, carbon dioxide and oxygenated hydrocarbons.

In another general embodiment, a system for removing impurities from a feed fluid comprising primarily a hydrocarbon comprises a vessel having an inlet and an outlet; a copper-based material in the vessel, the copper-based material being for removing oxygen from a feed fluid entering the vessel through the inlet; and an adsorbent in the vessel, the adsorbent being for removing at least one of water, carbon dioxide and oxygenated hydrocarbons from the feed fluid passing through the vessel.

In yet another general embodiment, a method for regenerating a single-vessel system for removing impurities from a feed fluid comprising primarily a hydrocarbon comprises contacting an oxidized copper-based material and an adsorbent in a single vessel with an inert gas heated to a first temperature above an ambient temperature for removing hydrocarbon adsorbed thereon; adding a reducing agent to the heated inert gas for reducing the copper-based material; increasing a concentration of reducing agent added in the heated inert gas contacting the copper-based material and the adsorbent; heating the inert gas and the reducing agent to a second temperature higher than the first temperature; and contacting the copper-based material and the adsorbent with the inert gas and the reducing agent at the second temperature.

Purification of Feed Fluid

Purification of feed fluids is carried out in a single vessel at ambient temperature. This has heretofore not been possible.

Standard purification of ethylene for a gas-phase polyethylene reactor may require removal of oxygen, carbon monoxide, water, carbon dioxide, and/or oxygenated hydrocarbons. Each of these impurities can be removed from ethylene in a single vessel using the teachings presented herein.

Figure 1:
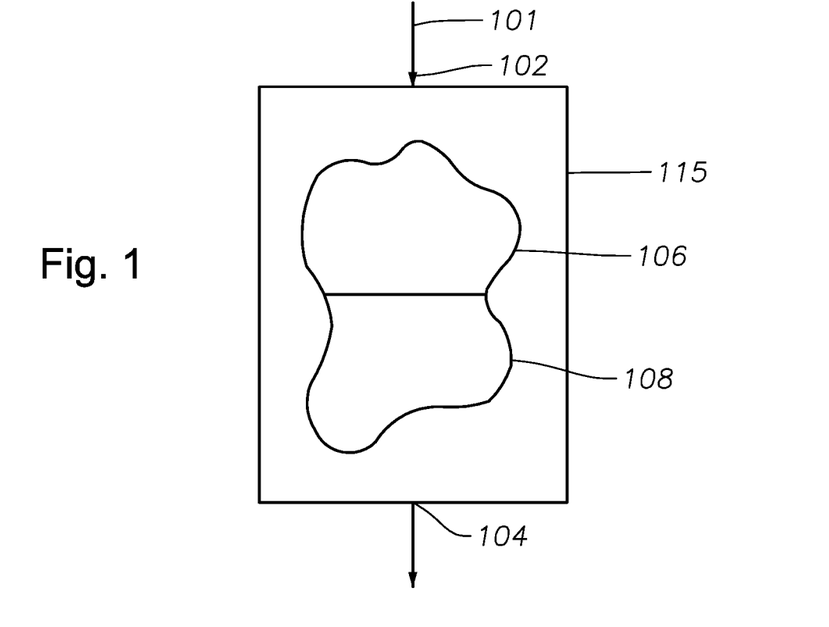
FIG. 1 is a schematic diagram of a system for removing impurities from a feed fluid according to one embodiment.

FIG. 1 schematically depicts an exemplary purification system for removing impurities according to one general embodiment comprises a vessel 115 having an inlet 102 and an outlet 104. A copper-based material 106 is positioned in the vessel 115, the copper-based material being for removing oxygen from a feed fluid 101 entering the vessel through the inlet 102. An adsorbent 108 in the vessel 115 removes at least one of water, carbon dioxide, and oxygenated hydrocarbons from the feed fluid passing through the vessel 115. In use, feed fluid is passed through the vessel and contacted with the copper-based material 106 and adsorbent 108 in the vessel 115. When appropriate, the copper-based material 106 and adsorbent 108 may be regenerated as set forth herein.

Figure 2:
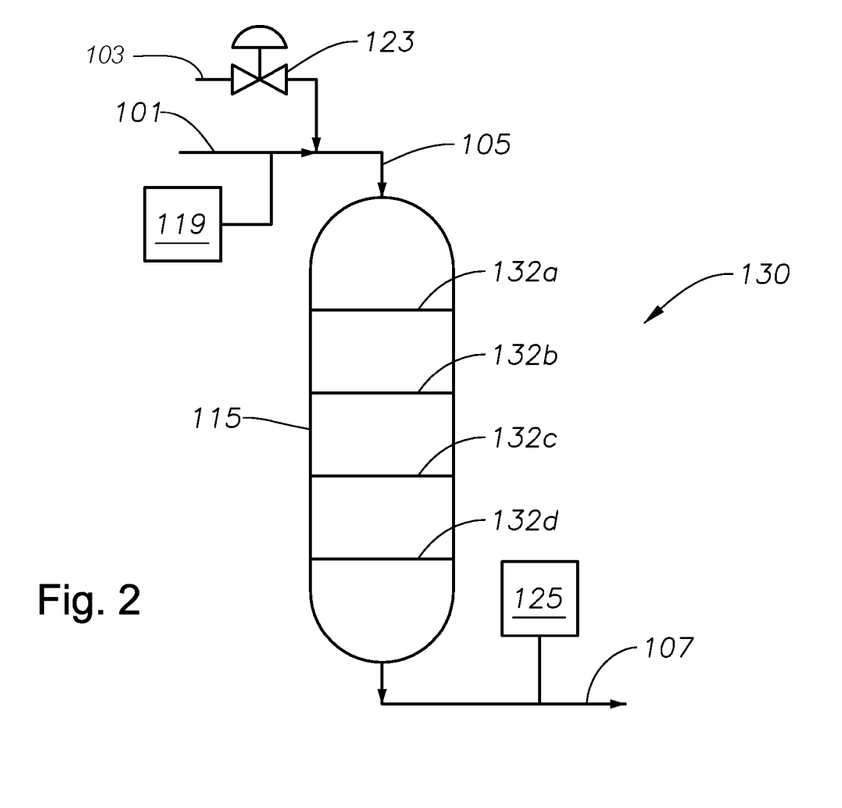
FIG. 2 is a schematic diagram of a system for removing impurities from a feed fluid in a single vessel according to one embodiment.

In an illustrative embodiment, shown in FIG. 2, a purification section 130 includes a single vessel 115 for removing one or more impurities such as oxygen, carbon monoxide, carbon dioxide, and/or water from a feed fluid 101. In this general embodiment, the single vessel 115 may contain one or more layers 132a-d of purification materials which each remove one or more impurities, such as carbon monoxide, oxygen, and water, from the feed fluid 101. Accordingly, each layer may include different materials. For example, a first layer may include a copper-based material, a second layer may include a molecular sieve, and a layer may include an alumina-based adsorbent. Further, some of the layers may include a mixture of purification materials.

In FIG. 2, there may be optionally a duplicate purification section located in parallel to section 130. This section would be placed into service when section 130 is undergoing regeneration.

Since the impurities can be removed at or near ambient temperatures, the embodiment of FIG. 2 does not require a pre-heater and a post cooler, though such devices may be present.

Referring to FIG. 2, optional purity analyzers 119 and 125 measure the amount of impurities present in the fluid upstream and downstream of the single vessel 115.

For reasons explained in more detail below, an oxygen containing fluid 103, the flowrate of which is controlled by adjusting the flow control valve 123, may be added upstream of the single vessel 115, or injected directly into the single vessel 115 through one or more injection ports.

With reference to FIGS. 1-2, the feed fluid 101 may include carbon monoxide and one or more additional impurities, such as oxygen and water for example, in an amount that exceeds the tolerance level of the polymerization catalyst. The carbon monoxide and other impurities are removed in the purification section 130. For example, the feed fluid 101 may comprise more than about 0.2 parts per million by volume (ppmv) of carbon monoxide, 0.1 ppmv of oxygen, and 0.3 ppmv of water. In one or more embodiments, the feed fluid 101 may include more than 1.0 ppmv of carbon monoxide, 0.5 ppmv of oxygen and 0.5 ppmv of water. In other embodiments, the feed fluid 101 may include about 0.2 ppmv to about 10 ppmv of carbon monoxide, about 0.1 ppmv to about 10 ppmv of oxygen, and of from about 0.3 ppmv to about 10 ppmv of water.

Removal of Carbon Monoxide and Oxygen From Feed Fluid

In one approach, oxygen may be removed from a feed fluid using a dispersed-copper-based material such as UT-2000™ (described below) at ambient temperature. Carbon monoxide may be removed with the same material by catalytic reaction with oxygen. If there is not a sufficient stoichiometric excess of oxygen in the feed fluid to effect a reaction of carbon monoxide to carbon dioxide, then oxygen may be added to the feed fluid.

Referring to FIG. 2, one class of embodiments are directed to a method of removing carbon monoxide and oxygen from a feed fluid by: providing a feed fluid 101 comprising oxygen and carbon monoxide; measuring an oxygen concentration and a carbon monoxide concentration in the feed fluid 101; combining an oxygen-containing fluid 103 with the feed fluid 101 to form a reacting fluid 105 wherein an amount of oxygen-containing fluid 103 combined with the feed fluid 101 is controlled to establish an $O_2/CO$ molar ratio in the reacting fluid 105 of greater than about 0.5:1; and passing the reacting fluid 105 over a reduced copper-based material at an operating temperature of less than about 40° C. (104° F.) to form a purified fluid 107, wherein oxygen and carbon monoxide contained in the reacting fluid 105 are reacted in the presence of the reduced copper-based material to form carbon dioxide.

In one particularly preferred embodiment, the copper-based material may be a copper-oxide catalyst such as UT-2000™ available from Univation Technologies, LLC (Houston, Tex.).

In any embodiment, other illustrative copper-based materials include copper-oxide catalysts such as POLYMAX 301 and POLYMAX 302 catalysts, which are commercially available from Süd-Chemie AG (Louisville, Ky.).

Other copper-oxide materials that may be used include R3-11, R3-15, and R3-16 materials sold by BASF Corp. (Florham Park, N.J.).

By removing the carbon monoxide and oxygen near ambient temperature, significant investment and energy savings are realized. For example, there is no need to pre-heat and thus post cool, thereby reducing both capital expenditures and operating expenses. Furthermore, a method for removing carbon monoxide and oxygen in a single catalyst bed or vessel, according to one embodiment, would further reduce capital and operating expenses associated with additional catalyst beds or vessels. In other embodiments, the carbon monoxide and oxygen may be removed at temperatures of less than about 35° C. (95° F.), less than about 30° C. (86° F.), or at temperatures between about 0° C. (32° F.) and about 40° C. (104° F.). In still other embodiments, the carbon monoxide and oxygen may be removed at temperatures of between about 0° C. (32° F.) and about 30° C. (86° F.).

In some embodiments of the invention, an oxygen-containing fluid 103 may be combined with the feed fluid 101 to form the reacting fluid 105 with sufficient oxygen present as required by the invention. The oxygen-containing fluid 103 may be combined with the feed fluid 101 to form the reacting fluid 105 upstream of the first packed bed 115. Alternately, the oxygen-containing fluid 103 may be introduced into the reaction zone of the packed bed via one or a plurality of oxygen injection points (not shown) located within the reaction zone. The oxygen-containing fluid 103 may be oxygen or any oxygen-containing fluid 103 that is compatible with the process.

In some embodiments, the amount of oxygen-containing fluid 103 combined with the feed fluid 101 may be controlled by controlling the flow of the oxygen-containing fluid 103. The desired flow of oxygen-containing fluid 103 may be determined by first measuring the flow rate of feed fluid 101, reacting fluid 105, purified fluid 107, e.g., a polymerization feed (provided the selected stream reflects the flow rate of reacting fluid 105 through the first packed bed 115), then using the measurements of oxygen and carbon monoxide concentration in the feed fluid 101 or reacting fluid 105 to determine the $O_2/CO$ molar ratio upstream of where the oxygen-containing fluid 103 is added. The flow rate of oxygen-containing fluid 103 to be added to achieve the desired $O_2/CO$ ratio in the reacting fluid 105 may then be determined. In a class of alternative embodiments, oxygen and carbon monoxide concentrations may be measured downstream. One means of adding a small amount of oxygen to the feed fluid 101 is by feeding dry instrument air boosted to sufficient pressure. A flow control valve 123, logic to control the amount of airflow, and appropriate safety equipment may be needed. In any embodiment, the $O_2/CO$ molar ratio in the reacting fluid 105 may be greater than an $O_2/CO$ ratio of about 0.5:1.

The amount of oxygen, if any, and the amount of carbon monoxide in the feed fluid 101 or in a reacting fluid 105 may be measured, for example, in real-time by an on-line feed purity analyzer 119, before the feed fluid 101 or reacting fluid 105 contacts the packed bed 115 (analyzer shown in FIG. 2 samples the feed fluid). The on-line feed purity analyzer 119 may be any analyzer or combination of more than one analyzer with the ability to measure oxygen and carbon monoxide at levels that may be found in the feed fluid 101. For example, the analysis of carbon monoxide in the feed fluid 101 may be carried out periodically, for example approximately every 2 to 15 minutes, using a gas chromatograph with flame ionization detector and methanator. Examples of analyzers for analysis of oxygen in the feed fluid 101 include the Delta F NANO Trace II and Teledyne Ultra Trace 3000, which have the ability to measure down to 0.001 ppmv oxygen in the gas phase, and are available commercially.

The reacting fluid 105 may then pass over a reduced copper-based material contained in the packed bed 115 at an operating temperature of less than about 40° C. (104° F.) to form a purified fluid 107. The oxygen and carbon monoxide contained in the reacting fluid 105 are reacted in the presence of the reduced copper-based material to form carbon dioxide. In other embodiments, the reacting fluid 105 may be passed over the reduced copper-based material at an operating temperature of less than about 35° C. (95° F.), less than about 30° C. (86° F.), or at operating temperatures between about 0° C. (32° F.) and about 40° C. (104° F.). In still other embodiments, the reacting fluid 105 may be passed over the reduced copper-based material at an operating temperature of between about 0° C. (32° F.) and about 30° C. (86° F.).

The oxygen and the carbon monoxide in the reacting fluid 105 may react in the presence of the reduced copper-based material in the first packed bed 115 to form carbon dioxide, thus removing oxygen and carbon monoxide from the reacting fluid 105 to form the purified fluid 107 that exits the packed bed 115. Without being bound to one particular theory, it is believed that the following reaction may occur:

[Equation 1]

$$CO + \tfrac{1}{2}O_2 \xrightarrow{Cu} CO_2$$

It is believed that as long as metallic copper is present, and oxygen is present, this catalyzed oxidation may occur. It was previously believed that the catalytic component for the reaction in Equation 1 was copper oxide (CuO).

[Equation 2]

$$CO + \tfrac{1}{2}O_2 \xrightarrow{CuO} CO_2$$

Further, the catalyzed reaction in Equation 2 was thought to require temperatures well above ambient to initiate.

As discussed above, a review in Katz, Morris, "Heterogeneous Oxidation of Carbon Monoxide," in *Advances in Catalysis*, Vol. V, p. 177 (1953) indicates that the oxidation of carbon monoxide by copper oxide, as shown in Equation 2, may not commence until about 200° C. (392° F.). This is why the conversion of carbon monoxide to carbon dioxide by reacting over copper according to Equation 1 at temperatures less than about 40° C. (104° F.) is surprising.

Thus, in any embodiment of the current invention, the reduced copper-based material may comprise a copper-oxide catalyst that is at least partly reduced to copper. The copper-based material may comprise one or more metals supported on a metal oxide carrier. Metals may include copper and other metals and/or oxides of other metals such as zinc, palladium, platinum, gold, and silver, as described in U.S. Pat. No. 6,278, 033. Thus, in any embodiment, the copper-based material may comprise copper oxide and zinc oxide. The copper-based materials may be reduced by treatment of the copper-based material with hydrogen at elevated temperature after being placed in the packed bed using procedures known in the art.

In one or more embodiments herein, the reduced copper-based material may also remove oxygen in the reacting fluid 105 by reaction of oxygen with the reduced copper-based material. The oxygen may combine with the reduced copper to form copper oxide as shown in Equation 3.

$$2Cu+O_2 \rightarrow 2CuO \quad \text{[Equation 3]}$$

In any embodiment, the first packed bed 115 may further include any additional material.

The purified fluid 107 exiting the first packed bed 115 will have most, if not essentially all, of the measurable carbon monoxide removed. In any embodiment, the purified fluid 107 may comprise less than about 0.20 ppmv carbon monoxide. In other embodiments, the purified fluid 107 may comprise less than about 0.10 ppmv carbon monoxide, or the purified fluid 107 may be absent of any measurable level of carbon monoxide.

Also, the purified fluid 107 exiting the first packed bed 115 will have most, if not essentially all, of the measurable oxygen removed. In one embodiment, the purified fluid 107 may comprise less than about 0.20 ppmv oxygen. In other embodiments, the purified fluid 107 may comprise less than about 0.10 ppmv oxygen, or the purified fluid 107 may be absent of any measurable level of oxygen.

Without being bound to one particular theory, it is believed that the carbon monoxide and oxygen react over the reduced copper-based material to remove the carbon monoxide by forming carbon dioxide according to Equation 1, and the oxygen reacts with the reduced copper-based material to remove the excess oxygen as shown in Equation 3. Thus, in one or more embodiments herein, the oxygen and carbon monoxide may be removed in a single bed of reduced copper-based material.

The copper-oxide formed by the oxidation of the copper can be later re-reduced using a regeneration stream comprising a reducing agent such as hydrogen. The regeneration stream carries off the removed oxygen as water, leaving behind a reduced metal ready for additional oxygen removal. Additional details can be found in U.S. Pat. Nos. 6,278,033 and 6,987,152, which are incorporated by reference. This combination of carbon monoxide and oxygen removal allows more oxygen to be present in the reacting fluid 105 than indicated by Equation 1 to react the oxygen and carbon monoxide to remove substantially all of the carbon monoxide. The net result is that in one or more embodiments herein, the purified fluid 107 may comprise less than about 0.20 ppmv of oxygen, less than about 0.10 ppmv of oxygen, or may be absent any measurable level of oxygen. Furthermore, the oxygen may be removed by the same catalyst as the carbon monoxide, for example in the same catalyst bed, at the same conditions, resulting in a purified effluent comprising less than about 0.2 ppm by volume oxygen, and less than about 0.2 ppm by volume carbon monoxide. In some embodiments, the purified fluid 107 may comprise less than about 0.10 ppmv of oxygen, and less than about 0.10 ppmv of carbon monoxide.

Another class of embodiments provides a method of removing carbon monoxide and oxygen from a feed fluid 101 comprising the steps of: providing a feed fluid 101 comprising carbon monoxide; combining an oxygen-containing fluid 103 with the feed fluid 101 to form a reacting fluid 105, wherein an amount of oxygen-containing fluid 103 combined with the feed fluid 101 is controlled in real-time to establish an $O_2/CO$ molar ratio in the reacting fluid 105 of greater than about 0.5:1; passing the reacting fluid 105 over the reduced copper-based material at an operating temperature of less than about 40° C. (104° F.) to form a purified fluid 107, wherein oxygen and carbon monoxide contained in the reacting fluid 105 are reacted in the presence of the reduced copper-based material to form carbon dioxide; measuring a real-time carbon monoxide concentration in the purified fluid 107; and increasing the amount of oxygen-containing fluid 103 combined with the feed fluid 101 in response to an increase over time in the real-time carbon monoxide concentration measured in the purified fluid 107. In this embodiment, the carbon monoxide concentration in the purified fluid 107 may be measured in real time by an on-line purified feed fluid analyzer 125 to determine how much, if any, carbon monoxide is coming through the first packed bed 115. The purified feed fluid analyzer 125 may be any impurity analyzer or combination of impurity analyzers with the ability to measure oxygen and carbon monoxide at levels that may be found in the purified fluid 107. If this analysis shows carbon monoxide is present, or shows the carbon monoxide in the purified fluid 107 increasing over time, then the amount of oxygen-containing fluid 103 being combined with the feed fluid 101 may be increased to increase the $O_2/CO$ ratio in the reacting fluid 105, and thus the removal of carbon monoxide in the first packed bed 115. The result is that the level of carbon monoxide passing through the first packed bed 115 will be decreased. In this method, it may be desirable to reduce the flow of oxygen-containing fluid 103 periodically to determine if the carbon monoxide in the purified fluid 107 returns.

It was found that the reaction of carbon monoxide with oxygen proceeds further by increasing the $O_2/CO$ ratio in the reacting fluid 105 above the stoichiometric levels, that is, above about 0.5:1. In addition, excess oxygen, for example, $O_2/CO$ ratios of greater than about 1:1, 2:1, 3:1, or 3.3:1, improve the removal of carbon monoxide from the reacting fluid 105. Furthermore, the reaction of carbon monoxide with oxygen proceeds further to completion at higher temperature and lower space velocity. An empirical model to quantify these relationships is:

$$\text{Fraction of CO removed} = 1 - \frac{1}{e^{[-2.261 - 0.866*(O2/CO)in - 0.032*T + 0.00065*SV - 0.14*(CO)in]}} \quad \text{[Equation 4]}$$

where T is temperature in ° C., SV is space velocity expressed as $h^{-1}$ (inverse hours), $(O_2/CO)_{in}$ is the molar ratio of oxygen to carbon monoxide in the reacting fluid 105, and $(CO)_{in}$ is the carbon monoxide concentration in the reacting fluid 105 expressed in units of ppmv. In some embodiments, $(CO)_{in}$ may also be carbon monoxide concentration in the feed fluid 101 expressed in units of ppmv, although this introduces a very small error in the results. Space velocity is the volumetric gas flow rate at 1 atmosphere and 21° C. (70° F.) divided by the packed bed volume. Equation 4 may be used to predict process conditions required to achieve desired purity levels in the purified fluid 107.

An example of how the fraction of CO removal is determined is as follows: a feed fluid 101 containing carbon monoxide at the limit of a typical ethylene specification of 5 ppmv may be assumed. Assuming a desired concentration of carbon monoxide in purified ethylene of less than about 0.2 ppmv, the fraction of carbon monoxide to be removed is 1−0.2/5=0.96.

Figure 3:
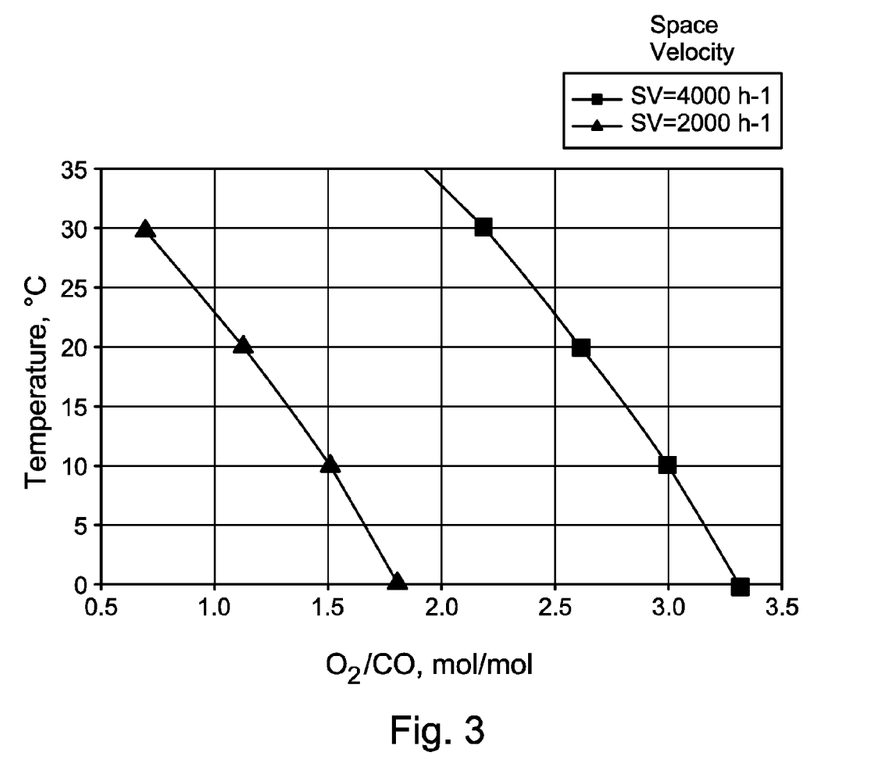
FIG. 3 is a chart plotting $O_2$/CO ratio versus temperature resulting in 96% carbon monoxide removal for space velocities of 4000 $h^{-1}$ and 2000 $h^{-1}$.

The combinations of temperature and $O_2/CO$ ratio needed to achieve carbon monoxide removal from the feed fluid containing 5 ppmv carbon monoxide in the feed fluid and less than about 0.2 ppmv carbon monoxide in the purified fluid is shown in FIG. 3. In FIG. 3, the feed fluid, for example ethylene, is assumed to comprise about 5 ppmv carbon monoxide, and the carbon monoxide in the purified fluid is selected to be less than about 0.2 ppmv. The combinations of temperature and $O_2/CO$ ratio needed to achieve this level (96%) of carbon monoxide removal are shown in FIG. 3 for space velocities of 4000 $h^{-1}$ and 2000 $h^{-1}$.

Thus, carbon monoxide in the feed fluid can be effectively removed, for example 96% removal, at a temperature as low as about 0° C. (32° F.) at high space velocity if enough oxygen, for example, an $O_2/CO$ ratio in the reacting fluid of greater than 3:1 or even 3.3:1, is present in the reacting fluid. At an operating temperature of about 20° C. (68° F.) or higher, an $O_2/CO$ ratio of no more than 2.6 is needed. If the first packed bed were designed such that space velocity were no greater than about 2000 $h^{-1}$, then the $O_2/CO$ ratio does not have to exceed about 1.1 at about 20° C. (68° F.). Thus, in any embodiments, the $O_2/CO$ molar ratio in the reacting fluid may be greater than about 1:1, 2:1, 3:1, or 3.3:1.

In one preferred embodiment, the reacting fluid is a gas, and a space velocity of the reacting fluid over the reduced copper-based material is between about 1,000 $h^{-1}$ to about 10,000 $h^{-1}$.

Given the correlations described above, and referring again to FIG. 2, in one class of embodiments, the invention provides a method of removing carbon monoxide and oxygen from a feed fluid 101 comprising the steps of: providing a feed fluid 101 comprising carbon monoxide; obtaining a real-time operating temperature of a reacting fluid 105; combining an oxygen-containing fluid 103 with the feed fluid 101 to form the reacting fluid 105, wherein an amount of oxygen-containing fluid 103 combined with the feed fluid 101 is determined in real time and controlled in real time based on the real-time operating temperature of the reacting fluid 105 passing over the reduced copper-based material, a specified carbon monoxide concentration in the feed fluid 101, and a real-time flow rate of the reacting fluid 105 over the reduced copper-based material; and passing the reacting fluid 105 over the reduced copper-based material to form a purified fluid 107, wherein oxygen and carbon monoxide contained in the reacting fluid 105 are reacted in the presence of the reduced copper-based material to form carbon dioxide. In this class of embodiments, the concentration of carbon monoxide in the feed fluid 101 is assumed to be at some specified level, for example, based on feed fluid 101 specifications, historical data, off-line measurements, or other method. The specified carbon monoxide level is then used in combination with the real-time operating temperature of the reacting fluid 105 and the space velocity through the bed of catalyst to determine the amount of oxygen that should be fed to the feed fluid 101. In one or more embodiments, the optimum amount of oxygen-containing fluid 103 to add to the feed fluid 101 is calculated by Equation 4.

Another class of embodiments provides a method for olefin polymerization, comprising: providing a feed fluid 101 comprising more than about 0.2 ppm by volume of carbon monoxide; measuring an oxygen concentration and a carbon monoxide concentration in the feed fluid 101; combining an oxygen-containing fluid 103 with the feed fluid 101 to form a reacting fluid 105, wherein an amount of oxygen-containing fluid 103 combined with the feed fluid 101 is controlled to establish an $O_2/CO$ molar ratio in the reacting fluid 105 of greater than about 0.5:1; passing the reacting fluid 105 over a reduced copper-based material at an operating temperature of less than about 40° C. (104° F.) to form a purified fluid 107, wherein the copper-based material comprises copper oxide and zinc oxide, wherein oxygen and carbon monoxide contained in the reacting fluid 105 are reacted in the presence of the reduced copper-based material to form carbon dioxide, and wherein the purified fluid 107 comprises less than about 0.2 ppmv of carbon monoxide; and passing the purified fluid 107 to a polymerization reactor. In a preferred embodiment, the reduced copper-based material removes oxygen in the reacting fluid 105 by reacting oxygen with the reduced copper-based material such that the purified fluid 107 comprises less than about 0.10 ppmv of oxygen, and wherein the reactions of $O_2$ with CO and copper occur in a single packed bed of reduced copper-based material.

In one or more embodiments, the preferred operating temperature of the feed fluid 101 may be determined based on the carbon monoxide and oxygen concentrations in the feed fluid 101, and a real-time flow rate of the feed fluid 101 or reacting fluid 105 over the reduced copper-based material. In these embodiments, the correlation described in Equation 4 may be used to determine the preferred operating temperature of the feed fluid 101.

Dehydration of Feed Fluid

Water may be removed by any desired mechanism. In particularly preferred embodiments, one or more adsorbents are used. As noted above, where multiple adsorbents are present in the single vessel, they may be in separate layers, mixed together, and combinations thereof. In a preferred mode, this part of the vessel includes a water-removal adsorbent such as 3A Molecular Sieves followed by modified alumina-based adsorbents. The alumina adsorbents can be, for example, Selexsorb COS and Selexsorb CD, which remove carbon dioxide and oxygenated hydrocarbons, respectively. In another mode, the molecular sieves are not present; the alumina-based adsorbents are used to also remove water. The drying material and/or alumina-based material also operate at ambient temperature.

With reference to FIG. 2, in one or more embodiments, adsorbent may be used to remove water and other impurities from a feed fluid 101 in a single vessel 115. The adsorbent may be a type that only removes water, such as 3A Molecular Sieves or 13X Molecular Sieves available commercially from many manufacturers. One or more layers 132a, 132b, etc., in the single vessel 115 may be comprised of molecular sieves to remove water from the feed fluid 101.

Generally, the term "molecular sieve" includes a wide variety of positive-ion-containing crystalline materials of both natural and synthetic varieties. They are generally characterized as crystalline aluminosilicates, although other crystalline materials are included in the broad definition. The crystalline aluminosilicates are made up of networks of tetrahedral of $SiO_4$ and $AlO_4$ moieties in which the silicon and aluminum atoms are cross-linked by the sharing of oxygen atoms. The electrovalence of the aluminum atom is balanced by the use of positive ions, for example, alkali-metal or alkaline-earth-metal cations.

Zeolitic materials, natural and synthetic, have been demonstrated in the art to have catalytic capabilities for many hydrocarbon processes. Zeolitic materials, often referred to as molecular sieves, are ordered porous crystalline aluminosilicates having a definite structure with large and small cavities interconnected by channels. The cavities and channels throughout the crystalline material are generally uniform in size allowing selective separation of hydrocarbons. Consequently, these materials in many instances have come to be classified in the art as molecular sieves and are utilized, in addition to the selective adsorptive processes, for certain catalytic properties. The catalytic properties of these materials are also affected, to some extent, by the size of the molecules which are allowed selectively to penetrate the crystal structure, presumably to be contacted with active catalytic sites within the ordered structure of these materials.

Prior art developments have resulted in the formation of many synthetic crystalline materials. Crystalline aluminosilicates are the most prevalent and are designated by letters or other convenient symbols. Exemplary of these materials are Zeolite A (Milton, in U.S. Pat. No. 2,882,243), Zeolite X (Milton, in U.S. Pat. No. 2,882,244), Zeolite Y (Breck, in U.S. Pat. No. 3,130,007), Zeolite ZSM-5 (Argauer, et al., in U.S. Pat. No. 3,702,886), Zeolite ZSM-11 (Chu, in U.S. Pat. No. 3,709,979), Zeolite ZSM-12 (Rosinski, et al., in U.S. Pat. No. 3,832,449), and others.

Manufacture of the ZSM materials utilizes a mixed base system in which sodium aluminate and a silicon containing material are mixed together with sodium hydroxide and an organic base, such as tetrapropylammonium hydroxide and tetrapropylammonium bromide, under specified reaction conditions, to form the crystalline aluminosilicate, preferably a crystalline metallosilicate exhibiting the MFI crystal structure.

In a preferred embodiment, the adsorbent is comprised of alumina-based materials such as SELEXSORB COS and SELEXSORB CD, capable of removing water plus carbon dioxide and oxygenated hydrocarbons, respectively. These adsorbents are available from Almatis AC, Inc. at the following address.

Almatis AC, Inc.
Adsorbents & Catalysts
15333 JFK Boulevard, Suite 425
Houston, Tex. 77032
(800)221-7392

Other alumina-based materials which may be used include AZ-300 and CG-731, which are available from UOP, located at the following address.

UOP LLC
25 East Algonquin Road
Des Plaines, Ill. 60017-5017

Preferred alumina-based materials may be hybrids of alumina and zeolite.

Figure 4:
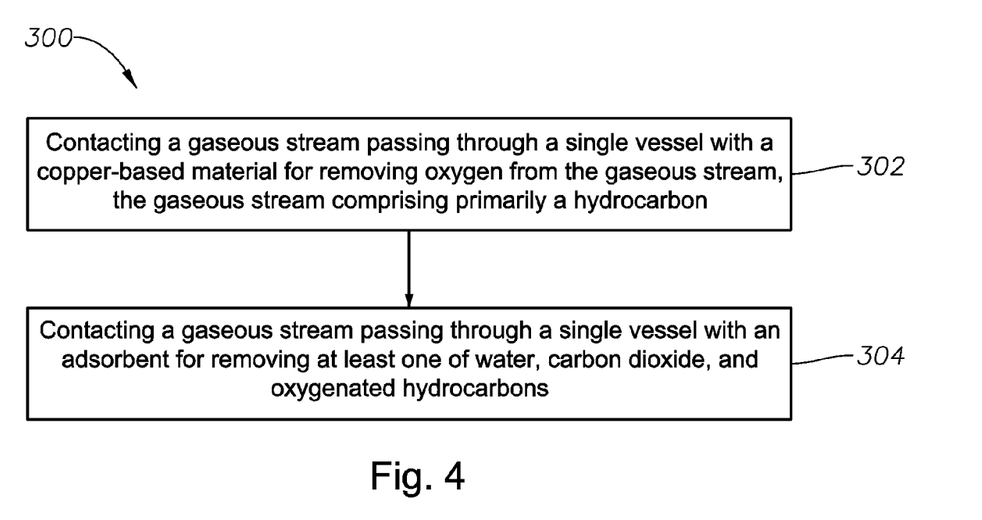
FIG. 4 is a flowchart of a method for removing impurities from a feed fluid according to one embodiment.

Now referring to FIG. 4, a method 300 for removing impurities from a feed fluid according to one embodiment is illustrated. As an option, the present method 300 may be implemented in the context of the functionality and architecture of FIGS. 1-2. Of course, however, the method 300 may be carried out in any desired environment. It should also be noted that the aforementioned definitions may apply during the present description.

In operation 302, a feed fluid passing through a single vessel is contacted with a copper-based material for removing oxygen from the feed fluid. In this embodiment, the feed fluid comprises primarily a hydrocarbon.

In a particularly preferred embodiment, the contacting is performed at about an ambient temperature.

In operation 304, the feed fluid passing through the single vessel is contacted with an adsorbent for removing at least one of the following: water, carbon dioxide, and oxygenated hydrocarbons.

In a preferred embodiment, the adsorbent further comprises a water-removing adsorbent, and removes carbon dioxide, water, and oxygenated hydrocarbons.

Given the dehydration capabilities of the adsorbents described above, and referring again to FIG. 2, in one class of embodiments, the invention provides a method of removing carbon monoxide, oxygen, and water from a feed fluid 101 in a single vessel 115 comprising the steps of: providing a feed fluid 101 comprising carbon monoxide; obtaining a real-time operating temperature of a reacting fluid 105; combining an oxygen-containing fluid 103 with the feed fluid 101 to form the reacting fluid 105, wherein an amount of oxygen-containing fluid 103 combined with the feed fluid 101 is determined in real time and controlled in real time based on the real-time operating temperature of the reacting fluid 105 passing over the reduced copper-based material, a specified carbon monoxide concentration in the feed fluid 101, and a real-time flow rate of the reacting fluid 105 over the reduced copper-based material; and passing the reacting fluid 105 over the reduced copper-based material to form a purified fluid 107, wherein oxygen and carbon monoxide contained in the reacting fluid 105 are reacted in the presence of the reduced copper-based material to form carbon dioxide.

In this class of embodiments, the concentration of carbon monoxide in the feed fluid 101 is assumed to be at some specified level, for example, based on feed fluid 101 specifications, historical data, off-line measurements, or other method. The specified carbon monoxide level is then used in combination with the real-time operating temperature of the reacting fluid 105 and the space velocity through the bed of catalyst 132a to determine the amount of oxygen that should be fed to the feed fluid 101. In one or more embodiments, the optimum amount of oxygen-containing fluid 103 to add to the feed fluid 101 is calculated by Equation 4. The reacting fluid is passed over the adsorbent bed 132b to remove water in the same vessel 115 that contains the copper-based material. Optionally, the adsorbent may be of a type that additionally removes at least one of carbon dioxide and oxygenated hydrocarbons.

Polymerization Systems

Embodiments of the invention described herein are suitable for use in any polymerization process that facilitates the contacting of the catalyst with a monomer or monomer plus comonomer. In one or more embodiments, the polymerization system may include solution, gas-phase fluidized bed, slurry phase, a high-pressure process, or a combination thereof. One or more embodiments may include gas-phase fluidized bed or slurry phase polymerization of one or more olefins at least one of which is ethylene or propylene. The gas phase process may be a process as described in U.S. Pat. Nos. 4,543,399, 4,588,790, 5,028,670, 5,317,036, 5,352,749, 5,405,922, 5,436,304, 5,453,471, 5,462,999, 5,616,661, or 5,668,228, all of which are fully incorporated herein by reference. The polymerization processes, particularly a gas-phase fluidized bed process, may comprise a cycle fluid that comprises a gas phase and a liquid phase.

In one or more embodiments, the method of this invention may be directed toward a solution, high pressure, slurry, or gas-phase polymerization process of one or more olefin monomers having from 2 to 30 carbon atoms, preferably 2 to 12 carbon atoms, and more preferably 2 to 8 carbon atoms. In a preferred embodiment, polymerization is of two or more olefin monomers such as ethylene, propylene, butene-1, pentene-1,4-methyl-pentene-1, hexene-1, octene-1 and decene-1.

In one or more embodiments, a copolymer of ethylene is produced, where with ethylene, a comonomer having at least one alpha-olefin having from 3 to 15 carbon atoms, from 4 to 12 carbon atoms, or from 4 to 8 carbon atoms, is polymerized in a gas phase process.

The reactor pressure in a gas phase process may vary from about 100 psig (690 kPa) to about 600 psig (4138 kPa), from about 200 psig (1379 kPa) to about 400 psig (2759 kPa), or from about 250 psig (1724 kPa) to about 350 psig (2414 kPa).

The reactor temperature in a gas-phase process during the contacting step may vary in a range of from about 30° C. (86° F.) to about 120° C. (248° F.), from about 60° C. (140° F.) to about 115° C. (239° F.), from about 70° C. (158° F.) to about 110° C. (230° F.), or from about 70° C. (158° F.) to about 95° C. (203° F.).

Other gas-phase processes contemplated by the method of the invention include series or multistage polymerization processes. Also gas-phase processes contemplated by the invention include those described in U.S. Pat. Nos. 5,627,242, 5,665,818 and 5,677,375, and European publications EP-A-0 794 200 EP-B1-0 649 992, EP-A-0 802 202 and EP-B-634 421, all of which are herein fully incorporated by reference.

In one or more embodiments, the invention is directed to a polymerization process, particularly a gas-phase or slurry phase process, for polymerizing propylene alone or with one or more other monomers including ethylene, and/or other olefins having from 4 to 12 carbon atoms. Polypropylene polymers may be produced using the bridged metallocene catalysts as described in U.S. Pat. Nos. 5,296,434 and 5,278,264, both of which are herein incorporated by reference. Propylene-based polymers that are produced in the method of the invention include atactic polypropylene, isotactic polypropylene, and syndiotactic polypropylene. Other propylene polymers include propylene random, block or impact copolymers.

In one or more embodiments, the polymerization may be by particle form polymerization, or a slurry process where the temperature is kept below the temperature at which the polymer goes into solution. Such technique is well known in the art, and described in for instance U.S. Pat. No. 3,248,179, which is fully incorporated herein by reference. Other slurry processes include those employing a loop reactor and those utilizing a plurality of stirred reactors in series, parallel, or combinations thereof. Non-limiting examples of slurry processes include continuous loop or stirred tank processes. Also, other examples of slurry processes are described in U.S. Pat. Nos. 4,613,484 and 5,986,021, which are herein fully incorporated by reference.

In other embodiments, the polymerization may be by solution processes as described in U.S. Pat. Nos. 4,271,060, 5,001,205, 5,236,998, 5,589,555 and 5,977,251, and PCT WO 99/32525 and WO 99/40130, which are fully incorporated herein by reference.

Catalyst Components and Catalyst Systems

Any polymerization catalyst suitable for use in the polymerizing olefins may be used as the polymerization process, including conventional transition metal catalysts, and metallocene catalysts.

Conventional transition metal catalysts are those traditional Ziegler-Natta catalysts and Phillips-type chromium catalyst well known in the art. Examples of conventional transition metal catalysts are discussed in U.S. Pat. Nos. 4,115,639, 4,077,904 4,482,687, 4,564,605, 4,721,763, 4,879,359 and 4,960,741, all of which are herein fully incorporated by reference. The conventional transition metal catalyst compounds that may be used in the present invention include transition metal compounds from Groups III to VIII, preferably IVB to VIB of the Periodic Table of Elements.

Still other conventional transition metal catalyst compounds and catalyst systems suitable for use in the present invention are disclosed in U.S. Pat. Nos. 4,124,532, 4,302,565, 4,302,566 and 5,763,723 and published EP-A2 0 416 815 A2 and EP-A 1 0 420 436, which are all herein incorporated by reference.

Other catalysts may include cationic catalysts such as $AlCl_3$, vanadium, constrained-geometry catalysts, cobalt, and iron catalysts, all being well known in the art.

Metallocene catalyst compounds and catalyst systems useful in the invention may include those described in U.S. Pat. Nos. 5,064,802, 5,145,819, 5,149,819, 5,243,001, 5,239,022, 5,276,208, 5,296,434, 5,321,106, 5,329,031, 5,304,614, 5,677,401, 5,723,398, 5,753,578, 5,854,363, 5,856,547 5,858,903, 5,859,158, 5,900,517, 5,939,503 and 5,962,718 and PCT publications WO 93/08221, WO 93/08199, WO 95/07140, WO 98/11144, WO 98/41530, WO 98/41529, WO 98/46650, WO 99/02540 and WO 99/14221 and EP-A-0 578 838, EP-A-0 638 595, EP-B-0 513 380, EP-A1-0 816 372, EP-A2-0 839 834, EP-B1-0 632 819, EP-B1-0 739 361, EP-B1-0 748 821 and EP-B1-0 757 996, all of which are herein fully incorporated by reference.

Other metallocene catalysts compounds useful in the invention may include metallocene compounds described in, for example, PCT publication WO 92/00333, WO 94/07928, WO 91/04257, WO 94/03506, WO96/00244, WO 7/15602 and WO 99/20637 and U.S. Pat. Nos. 5,057,475, 5,096,867, 5,055,438, 5,198,401, 5,227,440, 5,264,405 and EP-A-0 420 436, all of which are herein fully incorporated by reference.

Furthermore, the metallocene catalyst compounds useful in the invention may include complexes of $Ni^{2+}$ and $Pd^{2+}$ described in the articles Johnson, et al., "New Pd(II)- and Ni(II)-Based Catalysts for Polymerization of Ethylene and α-Olefins", *J. Am. Chem. Soc.*, (1995) 117, 6414-6415 and Johnson et al., "Copolymerization of Ethylene and Propylene with Functionalized Vinyl Monomers by Palladium(II) Catalysts", *J. Am. Chem. Soc.*, (1996) 118, 267-268, and WO 96/23010, WO 99/02472, U.S. Pat. Nos. 5,852,145, 5,866,663 and 5,880,241, which are all herein fully incorporated by reference.

Also included as metallocene catalyst are those diimine based ligands of Group 8 to 10 metal compounds disclosed in WO 96/23010 and WO 97/48735 and Gibson et al., *Chem. Comm.*, pp. 849-850 (1998), all of which are herein incorporated by reference.

Other metallocene catalysts are those Group 5 and 6 metal imido complexes described in EP-A2-0 816 384 and U.S. Pat. No. 5,851,945, which is incorporated herein by reference. In addition, metallocene catalysts include bridged bis(arylamido) Group 4 compounds described by D. H. McConville et al., in *Organometallics,* 1195, 14, 5478-5480, which is herein incorporated by reference. In addition, bridged bis(amido) catalyst compounds are described in WO 96/27439, which is herein incorporated by reference. Other metallocene catalysts are described as bis(hydroxy aromatic nitrogen ligands) in U.S. Pat. No. 5,852,146, which is incorporated herein by reference. Other metallocene catalysts containing one or more Group 15 atoms include those described in WO 98/46651, which is herein incorporated herein by reference. Still another metallocene catalysts include those multinuclear metallocene catalysts as described in WO 99/20665, which is incorporated herein by reference.

It is also contemplated that the metallocene catalysts described above may include their structural or optical or enantiomeric isomers (meso and racemic isomers, for example see U.S. Pat. No. 5,852,143, incorporated herein by reference) and mixtures thereof.

Regeneration of Feed Fluid Purification System

After the feed fluid has been substantially purified, there may be byproducts and residual contaminants in the Feed Fluid Purification System such as copper-oxide (CuO), oxygenated hydrocarbons, carbon dioxide, etc. Accordingly, it is preferable to regenerate the system periodically to achieve high efficiencies in purifying the feed fluid.

Figure 5:
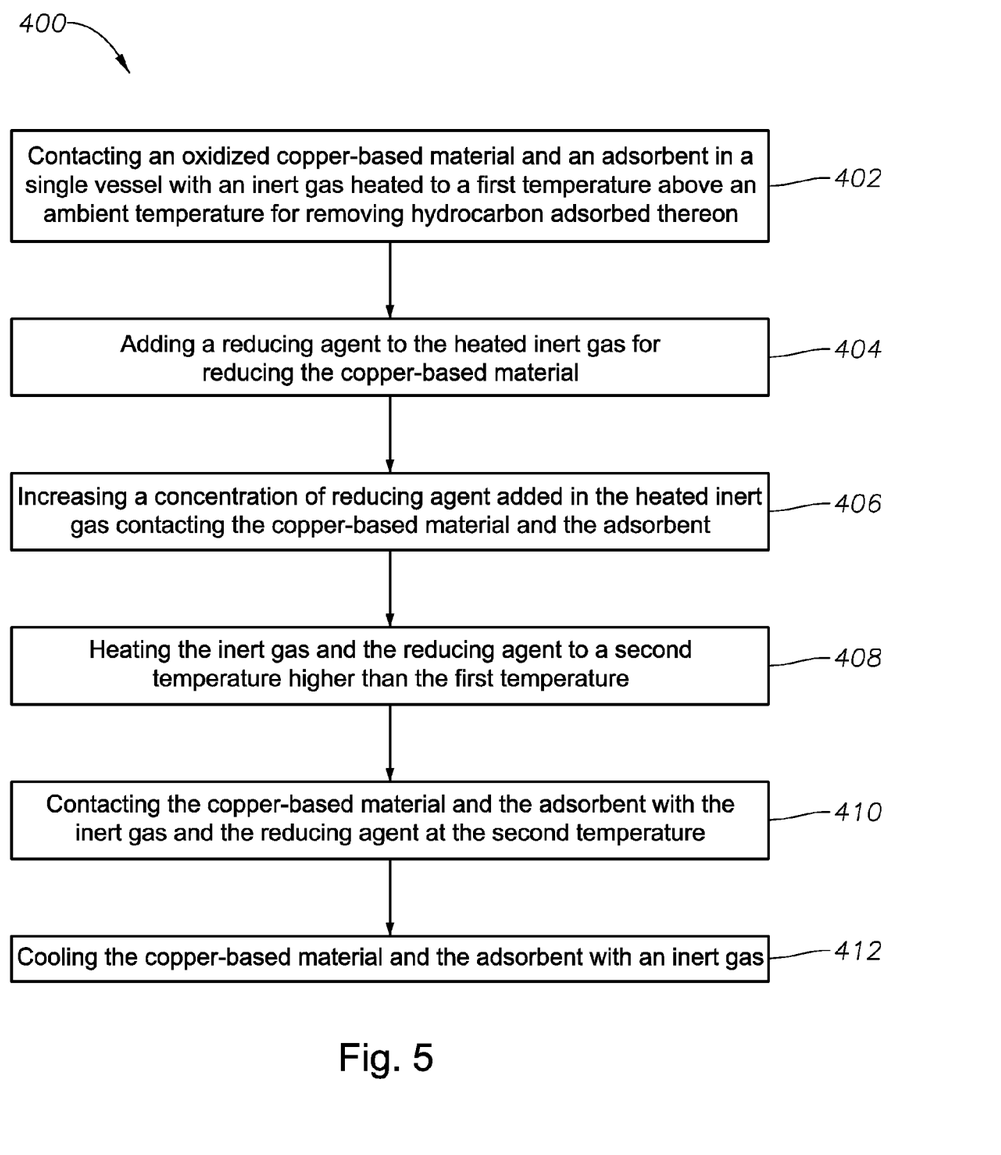
FIG. 5 is a flowchart of a method for regenerating a system for removing impurities from a feed fluid according to one embodiment.

FIG. 5 illustrates a method 400 for regenerating a system for removing impurities from a feed fluid according to one embodiment. It should be noted that the aforementioned definitions may apply during the present description.

In operation 402, an oxidized copper-based material and an adsorbent in a single vessel is contacted with an inert gas heated to a first temperature above an ambient temperature for removing hydrocarbon adsorbed thereon. The inert gas may be any non-reactive gas such as nitrogen, argon, helium, etc.

In a preferred embodiment, the first temperature is at least about 150° C. (302° F.).

In operation 404, a reducing agent is added to the heated inert gas for reducing the copper-based material. The reducing agent may be any reducer that is easily oxidized such as hydrogen.

In operation 406, a concentration is increased of the reducing agent added in the heated inert gas contacting the copper-based material and the adsorbent. The increase in concentration of the reducing agent should correlate to providing an amount of reducing agent that can substantially reduce the copper-based material.

In operation 408, the inert gas and the reducing agent are heated to a second temperature higher than the first temperature.

In one approach, the second temperature is about 210-250° C. (410-482° F.).

In a preferred embodiment, to avoid prolonged regeneration times, the second temperature is about 230-250° C. (446-482° F.).

In operation 410, the copper-based material and the adsorbent are contacted with the inert gas and the reducing agent at the second temperature. In this operation the system is regenerated, and contact should continue until the copper-based material is substantially reduced and the adsorbent is purged of impurities.

In one example of a particularly preferred regeneration procedure, heated nitrogen is passed upward through the single vessel, which is the opposite direction from flow of the feed fluid during its purification. Thus, the nitrogen contacts the adsorbents first and the copper-based material last. Optionally, the heated nitrogen may be allowed to cool down slightly before it reaches the copper-based material. Adsorbed hydrocarbons are driven out of the component materials using nitrogen heated to 150° C. Then, a controlled amount of hydrogen is fed into the vessel to initiate reduction of the copper-based material. In the next step, the temperature of the nitrogen plus hydrogen is increased to about 210° to about 250° C. At this time, the hydrogen concentration is increased until reduction of the copper-based material is complete. Then, the hydrogen flow is stopped. Depending on the temperature, regeneration of the drying material and the alumina material may be complete at this time. At temperatures less than 250° C., regeneration time for the drying and alumina materials will be lengthened and drying time may need to be extended. Following regeneration, the materials in the bed are preferably cooled with nitrogen or other inert gas. See operation 412. Note that the gas used for cooling may be the same gas used in one or more steps of the method 400, or may be a different lot, a different type, etc.

The phrases, unless otherwise specified, "consists essentially of" and "consisting essentially of" do not exclude the presence of other steps, elements, or materials, whether or not, specifically mentioned in this specification, as long as such steps, elements, or materials, do not affect the basic and novel characteristics of the invention, additionally, they do not exclude impurities and variances normally associated with the elements and materials used.

For the sake of brevity, only certain ranges are explicitly disclosed herein. However, ranges from any lower limit may be combined with any upper limit to recite a range not explicitly recited, as well as, ranges from any lower limit may be combined with any other lower limit to recite a range not explicitly recited, in the same way, ranges from any upper limit may be combined with any other upper limit to recite a range not explicitly recited. Additionally, within a range includes every point or individual value between its end points even though not explicitly recited. Thus, every point or individual value may serve as its own lower or upper limit combined with any other point or individual value or any other lower or upper limit, to recite a range not explicitly recited.

All priority documents are herein fully incorporated by reference for all jurisdictions in which such incorporation is permitted and to the extent such disclosure is consistent with the description of the present invention. Further, all documents and references cited herein, including testing procedures, publications, patents, journal articles, etc. are herein fully incorporated by reference for all jurisdictions in which such incorporation is permitted and to the extent such disclosure is consistent with the description of the present invention.

While the invention has been described with respect to a number of embodiments, those skilled in the art, having benefit of this disclosure, will appreciate that other embodiments can be devised which do not depart from the scope and spirit of the invention as disclosed herein.

What is claimed is:

1. A method for removing impurities from a feed fluid to a polymerization process, the feed fluid comprising primarily a hydrocarbon, the method comprising contacting the feed fluid in a single vessel with:
    a copper-based material for removing oxygen from the feed fluid; and
    multiple adsorbents for removing one or more of water, carbon dioxide, and oxygenated hydrocarbons from the feed fluid, wherein at least two of the adsorbents are different; and
    then using the purified feed fluid as a feed fluid to a polymerization process.

2. The method of claim 1, wherein the contacting is performed at about an ambient temperature.

3. The method of claim 1, wherein the feed fluid passes through multiple oxidation states of the copper-based material.

4. The method of claim 1, wherein at least one of the adsorbents comprises a molecular sieve component and an alumina-based adsorbent component.

5. The method of claim 1, wherein the feed fluid comprises oxygen and carbon monoxide, and further comprising adding oxygen to the feed fluid for increasing the molar ratio of oxygen to carbon monoxide in the feed fluid.

6. The method of claim 1, wherein the feed fluid comprises an olefin.

7. The method of claim 1, wherein the feed fluid comprises ethylene.

8. The method of claim 1, wherein the copper-based material is a copper-oxide catalyst.

9. The method of claim 1, wherein the multiple adsorbents are present in the single vessel in separate layers or are mixed together.

10. The method of claim 1, wherein the purified feed fluid is stored prior to being used as a feed fluid to a polymerization process.

11. The method of claim 1, wherein at least one of the adsorbents removes carbon dioxide and oxygenated hydrocarbons, and wherein at least one of the adsorbents removes water.

12. The method of claim 1, wherein at least one of the adsorbents is a molecular sieve, and wherein at least one of the other adsorbents is an alumina-based adsorbent.

13. The method of claim 12, wherein the feed fluid contacts the molecular sieve prior to contacting the alumina-based adsorbent.

\* \* \* \* \*